US005891318A

United States Patent [19]
Freire et al.

[11] Patent Number: 5,891,318
[45] Date of Patent: Apr. 6, 1999

[54] PRODUCTION OF ETHYLENE DICHLORIDE BY DIRECT CHLORINATION AND PRODUCTION OF VINYL CHLORIDE MONOMER USING CHLORINE RECYCLE AND APPARATUS

[75] Inventors: Francisco Jose Freire; Bruce Arthur Kaiser; Dennie Turin Mah, all of Wilmington, Del.; Vinci Martinez Felix, Kennett Square, Pa.

[73] Assignee: E. I. du Pont de Nemours and Company, Wilmington, Del.

[21] Appl. No.: 771,497

[22] Filed: Dec. 23, 1996

Related U.S. Application Data

[60] Provisional application No. 60/009,515, Dec. 28, 1995.
[51] Int. Cl.$^6$ .............................. C25B 3/06; C25B 9/00; C25B 15/08; C25B 1/26
[52] U.S. Cl. .......................... 205/349; 205/459; 205/620; 204/265; 204/266
[58] Field of Search .................................. 204/265, 266; 205/620, 637, 349, 459

[56] References Cited

U.S. PATENT DOCUMENTS

| | | | |
|---|---|---|---|
| 2,719,822 | 10/1955 | Kassel | 205/620 X |
| 5,411,641 | 5/1995 | Trainham, III et al. | 204/59 R |
| 5,635,052 | 6/1997 | Friere et al. | 205/349 X |

FOREIGN PATENT DOCUMENTS

| | | |
|---|---|---|
| 0 260 650 | 3/1988 | European Pat. Off. . |
| 7-216570 | 8/1995 | Japan .............................. C25B 1/26 |
| WO 95/14797 | 6/1995 | WIPO . |

OTHER PUBLICATIONS

Riegel (Edited by Kent, James A.), *Handbook of Industrial Chemistry,* Seventh Edition, Van Nostrand Reinhold Company (1974), pp. 783–785, (No Month).

Eames, D.J. et al., "Electrochemical Conversion of Anhydrous HC1 to CL$_2$ Using a Solid–Polymer–Electrolyte Electrolysis Cell", *Interface,* vol. 3, No. 1, Abstract, Douglas N. Bennion Memorial Symposium, The Electrochemical Society, Spring, 1994 No month.

Eames, D.J. et al., "Electrochemical Conversion of Anhydrous HC1 to CL$_2$ Using a Solid–Polymer–Electrolyte Electrolysis Cell", Presentation at the Douglas N. Bennion Memorial Symposium, 185$^{th}$ Meeting, The Electrochemical Society, Inc., San Francisco, CA, May 25, 1994.

Eames, D.J., "Production of Chlorine from Anhydrous Hydrogen Chloride in a Solid–Polymer–Electrolyte Cell", Thesis, University of California, Berkeley catalogued Dec. 13, 1994, pp. 1–93.

Eames, D.J. et al., "Electrochemical Conversion of Anhydrous HC1 to CL$_2$ Using a Solid–Polymer–Electrolyte Electrolysis Cell", (Jan. 16, 1995), pp. 322–336.

Schneiders, K., et al., "Recycle of HC1 to Chlorine", *Chlorine Institute,* Houston, Texas, May, 1995, pp. 1–26.

R.D. Villwock et al., "Recovery of Chlorine from Waste Anhydrous Hydrogen Chloride in a Membrane Electrolysis Cell", Presentation at 187th Electrochemical Society Meeting, Reno, Nevada, May 22, 1995.

(List continued on next page.)

*Primary Examiner*—Donald R. Valentine

[57] ABSTRACT

A process and a system uses a direct chlorination reactor for producing ethylene dichloride by direct chlorination, without the need for an oxychlorination unit. This ethylene dichloride may be used to make vinyl chloride monomer. In the process for making ethylene dichloride, ethylene and chlorine are both supplied to a direct chlorination reactor. The ethylene reacts with the chlorine to form ethylene dichloride. Chlorine is supplied to the direct chlorination reactor from an electrochemical cell which converts anhydrous hydrogen chloride to dry chlorine gas. This chlorine gas is purified and liquefied to form liquid dry chlorine, and the liquid dry chlorine is recycled to the direct chlorination reactor. The ethylene dichloride may be pyrolyzed to produce vinyl chloride monomer and anhydrous hydrogen chloride.

17 Claims, 4 Drawing Sheets

OTHER PUBLICATIONS

Tatapudi, P., et al., "Electrochemical Conversion of Anhydrous Hydrogen Chloride to Chlorine in a Proton Exchange Membrane Reactor", Los Alamos National Laboratory, Los Alamos, New Mexico, Presentation at 187th Electrochemical Society Meeting, Reno, Nevada, May 21–26, 1995; published in the Proceedings on the Symposium on *Water Purification by Photocatalytic, Photoelectrochemical and Electrochemical Processes,* vol. 95, No. 12 (1995).

Eames, D.J. et al., "Electrochemical Conversion of Anhydrous HC1 to $Cl_2$ Using a Solid Polymer Electrolyte Electrolysis Cell", *J. Electrochem. Soc.,* vol. 42, No. 11, (Nov. 1995), pp. 3619–3625.

PRODUCTION OF ETHYLENE DICHLORIDE BY DIRECT CHLORINATION AND PRODUCTION OF VINYL CHLORIDE MONOMER USING CHLORINE RECYCLE AND APPARATUS

This application claims the priority benefit of U.S. Provisional Application 60/009,515, filed Dec. 28, 1995.

BACKGROUND OF THE INVENTION

1. Field of the Invention

The present invention relates to a process and a system for producing ethylene dichloride by direct chlorination, and for producing vinyl chloride monomer from this ethylene dichloride using chlorine recycle.

2. Description of the Related Art

Ethylene dichloride (EDC) has value as a chemical intermediate. See Riegel's *Handbook of Industrial Chemistry*, Seventh Edition, Van Nostrand Reinhold Company, pp. 783–785. Most of the EDC produced goes into the manufacture of vinyl chloride monomer (VCM). Vinyl chloride monomer, $CH_2=CHCl$, by virtue of the wide range of applications for its polymers in both flexible and rigid forms, is one of the largest commodity chemicals in the United States and is an important item of international commerce. See Kirk Othmer, *Encyclopedia of Chemical Technology*, Third edition, Volume 23, pp. 865–866 (1983). For instance, vinyl chloride monomer is used to make poly(vinyl chloride).

Hydrogen chloride (HCl), in either anhydrous form or aqueous form (also referred to as hydrochloric acid), is a reaction by-product of many manufacturing processes which use chlorine. For example, chlorine is used to manufacture polyvinyl chloride, isocyanates, and chlorinated hydrocarbons/fluorinated hydrocarbons, with hydrogen chloride as a by-product of these processes. Because supply so exceeds demand, hydrogen chloride, or hydrochloric acid, often cannot be sold or used, even after careful purification. Shipment over long distances is not economically feasible. Discharge of the chloride ions or the acid into waste water streams is environmentally unsound. Recovery and feedback of the chlorine to the manufacturing process is the most desirable route for handling the HCl by-product.

Direct chlorination is a known process for making VCM. However, this process does not recover and feed the chlorine back to the VCM manufacturing process, and therefore, it is not used commercially. Because of the environmental considerations which make recovering and feeding chlorine back to a manufacturing process which uses chlorine particularly desirable, a balanced process using an oxychlorination process has been developed to make vinyl chloride from ethylene dichloride. In a typical plant producing vinyl chloride from ethylene dichloride, HCl is produced through pyrolysis of ethylene dichloride, and all the HCl produced in this pyrolysis is normally used as the feed for oxychlorination. In this process, EDC production is about evenly split between direct chlorination and oxychlorination, and there is no net production or consumption of HCl.

Figure 1:
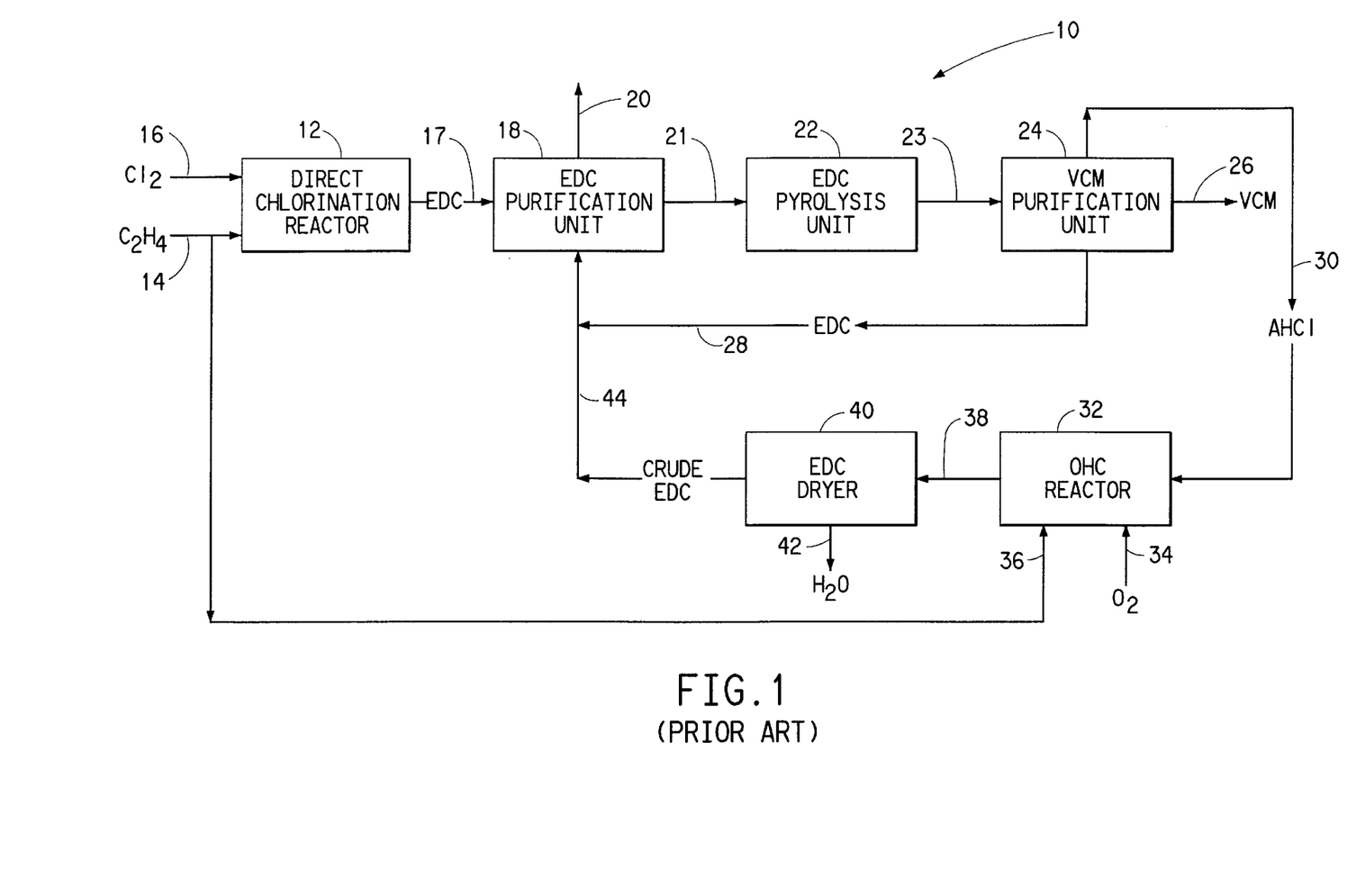
FIG. 1 is a block flow diagram showing a system for producing ethylene-based vinyl chloride production according to the prior art.

A plant, or system, employing a currently used balanced oxychlorination process for ethylene-based vinyl chloride production is illustrated in the block flow diagram of FIG. 1. The plant is shown generally at 10. Plant 10 includes a direct chlorination reactor as shown at 12 in FIG. 1. A first inlet feed line 14 as shown in FIG. 1 feeds ethylene ($C_2H_4$) to the direct chlorination reactor. A second inlet feed line 16 feeds chlorine ($Cl_2$) to the direct chlorination reactor. The ethylene and the chlorine are reacted in the reactor to produce ethylene dichloride (EDC). The EDC is sent through a line 17 to an ethylene dichloride (EDC) purification unit 18.

The EDC purification unit purifies the ethylene dichloride, and light and heavy ends, which are a by-product of this purification, are released through a line 20 as shown in FIG. 1. Plant 10 also includes an ethylene dichloride (EDC) pyrolysis unit 22 as shown in FIG. 1. The purified EDC is delivered to the pyrolysis unit through a line 21. The pyrolysis unit pyrolyzes the ethylene dichloride to produce vinyl chloride monomer (VCM) and essentially anhydrous hydrogen chloride, which are both sent to a vinyl chloride monomer (VCM) purification unit 24 through a line 23 as shown in FIG. 1. The VCM purification unit separates the VCM and the essentially anhydrous hydrogen chloride. The VCM is sent through a line 26 for further purification. A portion of the EDC is unreacted in the pyrolysis unit, and may be recycled back to the EDC purification unit from the VCM purification unit through a line 28. The essentially anhydrous hydrogen chloride is sent through a line 30 as shown in FIG. 1 to an oxychlorination reactor 32. Oxygen is added to the oxychlorination reactor through a line 34 as shown in FIG. 1. In addition, ethylene ($C_2H_4$) from first inlet feed line 14 is added to the oxychlorination unit through a line 36. Crude EDC, which has many impurities, and water are formed in the oxychlorination reactor, which are sent through a line 38 to an ethylene dichloride (EDC) dryer 40 as shown in FIG. 1. The EDC is dried in the EDC dryer, and the water resulting from this drying is released from the EDC dryer through a line 42. The crude EDC from the EDC dryer is sent through a line 44 back to the EDC purification unit.

Ethylene dichloride made from the oxychlorination process is generally less pure (~93 wt. % yield) than EDC produced by direct chlorination and, thus, is usually washed with water and then with caustic solution to remove water-extractable impurities. In contrast, direct chlorination generally produces EDC with a purity greater than 99.5 wt. % and, except for removal of the catalyst used in the formation of ethylene dichloride, such as ferric chloride, little further purification is necessary. Moreover, compared with direct chlorination, the oxychlorination process is characterized by higher capital investment and higher operating costs and less pure EDC product. However, the use of the oxychlorination process is dictated by the need to consume the HCl generated in EDC pyrolysis.

Therefore, there exists a need to develop a system and a process for producing EDC by direct chlorination. Such a system and process could be used to make a wide variety of products from the EDC, including, in particular VCM. The VCM manufacturing process produces anhydrous hydrogen chloride (AHCl), which is difficult to dispose of, as noted above. Therefore, the need also exists to develop a system and a process for producing VCM which is able to use the AHCl from this process and recycle the chlorine from this AHCl back to the VCM manufacturing process.

SUMMARY OF THE INVENTION

The present invention solves the problems of the prior art by providing a process and a system for manufacturing EDC by direct chlorination. This EDC may be used in a process for making VCM which recycles chlorine to the VCM manufacturing process and which eliminates the need for an oxychlorination unit or an EDC dryer. This results in less capital investment and lower operating costs in producing EDC or VCM as compared to processes and systems of the prior art.

Moreover, since the process and the system of the present invention produce EDC by direct chlorination alone, and not by oxychlorination, the EDC produced by the present invention is much cleaner, i.e., it has much less light and heavy ends, than that produced by the prior art. This results in a much purer product (i.e., purity greater than 99.5 wt. %, as opposed to about 93 wt. % for oxychlorination). In addition, less processing is necessary to achieve this purer product. Furthermore, by producing much purer EDC, the process and system of the present invention reduce the formation of undesirable by-products and thus the cost of disposal of such by-products.

In addition, the oxychlorination process of the prior art consumes oxygen, thus adding expense to the process. In contrast, the process and the system of the present invention produce hydrogen, a valuable commodity, thereby increasing the profitability of making EDC or VCM.

Thus, for all these reasons, the process and system of the present invention are more economical than processes and systems of the prior art for producing EDC or VCM. In addition, the process and system of the present invention are more environmentally acceptable than prior art processes and systems for manufacturing VCM, since they minimize or eliminate the environmental problems associated with the disposal of undesirable by-products in the VCM manufacturing process, such as anhydrous hydrogen chloride.

To achieve the foregoing solutions, and in accordance with the purposes of the invention as embodied and broadly described herein, there is provided a system for producing ethylene dichloride from chlorine gas produced by the electrochemical conversion of anhydrous hydrogen chloride, comprising: a direct chlorination reactor; a first inlet supply line for supplying ethylene to the direct chlorination reactor; a second inlet supply line for supplying chlorine to the direct chlorination reactor, wherein the ethylene and the chlorine react in the direct chlorination reactor to produce ethylene dichloride; and an electrochemical cell including means for oxidizing anhydrous hydrogen chloride to produce dry chlorine gas and protons, an anode chamber disposed adjacent the oxidizing means, anode-side inlet means disposed in fluid communication with the anode chamber for introducing the anhydrous hydrogen chloride to the oxidizing means and anode-side outlet means also disposed in fluid communication with the anode chamber for discharging the chlorine gas, cation-transporting means for transporting the protons therethrough, wherein the oxidizing means is disposed in contact with one side of the cation-transporting means, means for reducing the transported protons, wherein the reducing means is disposed in contact with the other side of the cation-transporting means, a cathode chamber disposed adjacent the reducing means, cathode-side inlet means disposed in fluid communication with the cathode chamber for introducing a fluid to the other side of the cation-transporting means and cathode-side outlet means also disposed in fluid communication with the cathode chamber; a purification unit for liquefying the chlorine gas to liquid dry chlorine; and a recycle line connected to the outlet means at one end thereof and to the second inlet supply line at the other end thereof for recycling the liquid dry chlorine to the direct chlorination reactor.

Further in accordance with the purposes of the invention, there is provided a system for producing vinyl chloride monomer from chlorine gas produced by the electrochemical conversion of anhydrous hydrogen chloride, comprising: a direct chlorination reactor; a first inlet supply line for supplying ethylene to the direct chlorination reactor; a second inlet supply line for supplying chlorine to the direct chlorination reactor, wherein the ethylene and the chlorine react in the direct chlorination reactor to produce ethylene dichloride; a pyrolysis unit for pyrolyzing the ethylene dichloride to produce vinyl chloride monomer; and an electrochemical cell including means for oxidizing anhydrous hydrogen chloride to produce dry chlorine gas and protons, an anode chamber disposed adjacent the oxidizing means, anode-side inlet means disposed in fluid communication with the anode chamber for introducing the anhydrous hydrogen chloride to the oxidizing means and anode-side outlet means also disposed in fluid communication with the anode chamber for discharging the chlorine gas, cation-transporting means for transporting the protons therethrough, wherein the oxidizing means is disposed in contact with one side of the cation-transporting means, means for reducing the transported protons, wherein the reducing means is disposed in contact with the other side of the cation-transporting means, a cathode chamber disposed adjacent the reducing means, cathode-side inlet means disposed in fluid communication with the cathode chamber for introducing a fluid to the other side of the cation-transporting means and cathode-side outlet means also disposed in fluid communication with the cathode chamber; a purifier for liquefying the chlorine gas to liquid dry chlorine; and a recycle line connected to the outlet means at one end thereof and to the second inlet supply line at the other end thereof for recycling the liquid dry chlorine to the direct chlorination reactor.

Further in accordance with the purposes of the invention, there is provided a process for producing ethylene dichloride from chlorine gas produced by the electrochemical conversion of anhydrous hydrogen chloride, comprising the steps of: supplying ethylene to a direct chlorination reactor; supplying chlorine to the direct chlorination reactor, wherein the ethylene reacts with the chlorine in the direct chlorination reactor to form ethylene dichloride; supplying anhydrous hydrogen chloride to an anode-side inlet of an electrochemical cell, wherein the electrochemical cell comprises a cation-transporting membrane, an anode disposed in contact with one side of the membrane and a cathode disposed in contact with the other side of the membrane; applying a voltage to the electrochemical cell so that the anode is at a higher potential than the cathode, and so that the anhydrous hydrogen chloride is oxidized at the anode to produce chlorine gas and protons, the chlorine gas is released from the cell, the protons are transported through the cation-transporting membrane of the cell, and the transported protons are reduced at the cathode of the cell; liquefying the chlorine gas to liquid dry chlorine; and recycling the liquid dry chlorine back to the direct chlorination reactor to produce ethylene dichloride.

Further in accordance with the present invention, there is provided a process for producing vinyl chloride monomer from chlorine gas produced by the electrochemical conversion of anhydrous hydrogen chloride, comprising the steps of supplying ethylene to a direct chlorination reactor; supplying chlorine to the direct chlorination reactor, wherein the ethylene reacts with the chlorine in the direct chlorination reactor to form ethylene dichloride; pyrolyzing the ethylene dichloride to produce vinyl chloride monomer and anhydrous hydrogen chloride; supplying the anhydrous hydrogen chloride to an anode-side inlet of an electrochemical cell, wherein the electrochemical cell comprises a cation-transporting membrane, an anode disposed in contact with one side of the membrane and a cathode disposed in contact with the other side of the membrane; applying a voltage to the electrochemical cell so that the anode is at a higher potential than the cathode and so that the anhydrous hydrogen chloride is oxidized at the anode to produce chlorine gas and protons, the chlorine gas is released from the cell, the protons are transported through the membrane of the cell, and the transported protons are reduced at the cathode of the cell; liquefying the chlorine gas to liquid dry chlorine and recycling the chlorine gas back to the direct chlorination reactor.

BRIEF DESCRIPTION OF THE DRAWINGS

The accompanying drawings, which are incorporated in and constitute a part of the specification, illustrate a presently preferred embodiment of the invention and, together with the general description given above and the detailed description of the preferred embodiment given below, serve to explain the principles of the invention.

DESCRIPTION OF THE PREFERRED EMBODIMENTS

Reference will now be made in detail to the present preferred embodiments of the invention as illustrated in the accompanying drawings.

In accordance with the present invention, there is provided a system for producing ethylene dichloride from chlorine gas produced by the electrochemical conversion of anhydrous hydrogen chloride. The system of the present invention is shown generally at 100 in FIG. 2. This electrochemical conversion directly converts essentially anhydrous hydrogen chloride to dry chlorine gas. The term "direct" means that the electrochemical cell obviates the need to convert the essentially anhydrous hydrogen chloride to aqueous hydrogen chloride before electrochemical treatment. By "anhydrous", or "essentially anhydrous", is meant that the hydrogen chloride is molecular in form, as opposed to aqueous hydrogen chloride, which is ionic in form.

The ethylene dichloride can be used to make various products. An example of such a product is vinyl chloride monomer, as will be described below. In addition, ethylene dichloride made by the present invention can be chlorinated to mainly tetrachloroethane; catalytic dehydrochlorination of the tetra gives trichloroethylene. With different chlorination conditions, mainly pentachloroethane can be formed, and with dehydrochlorination, perchloroethylene can be formed. Another modification of EDC chlorination is to adjust the conditions to maximize 1,1,2-trichloroethane as the product. This product, when dehydrochlorinated gives vinylidene chloride (1,1-dichloroethylene), a monomer used in a growing number of plastic polymers. This vinylidene chloride can be hydrochlorinated to methyl chloroform. The EDC produced by the present invention can also be used as a lead scavenger, or to produce ethylene amines.

Figure 2:
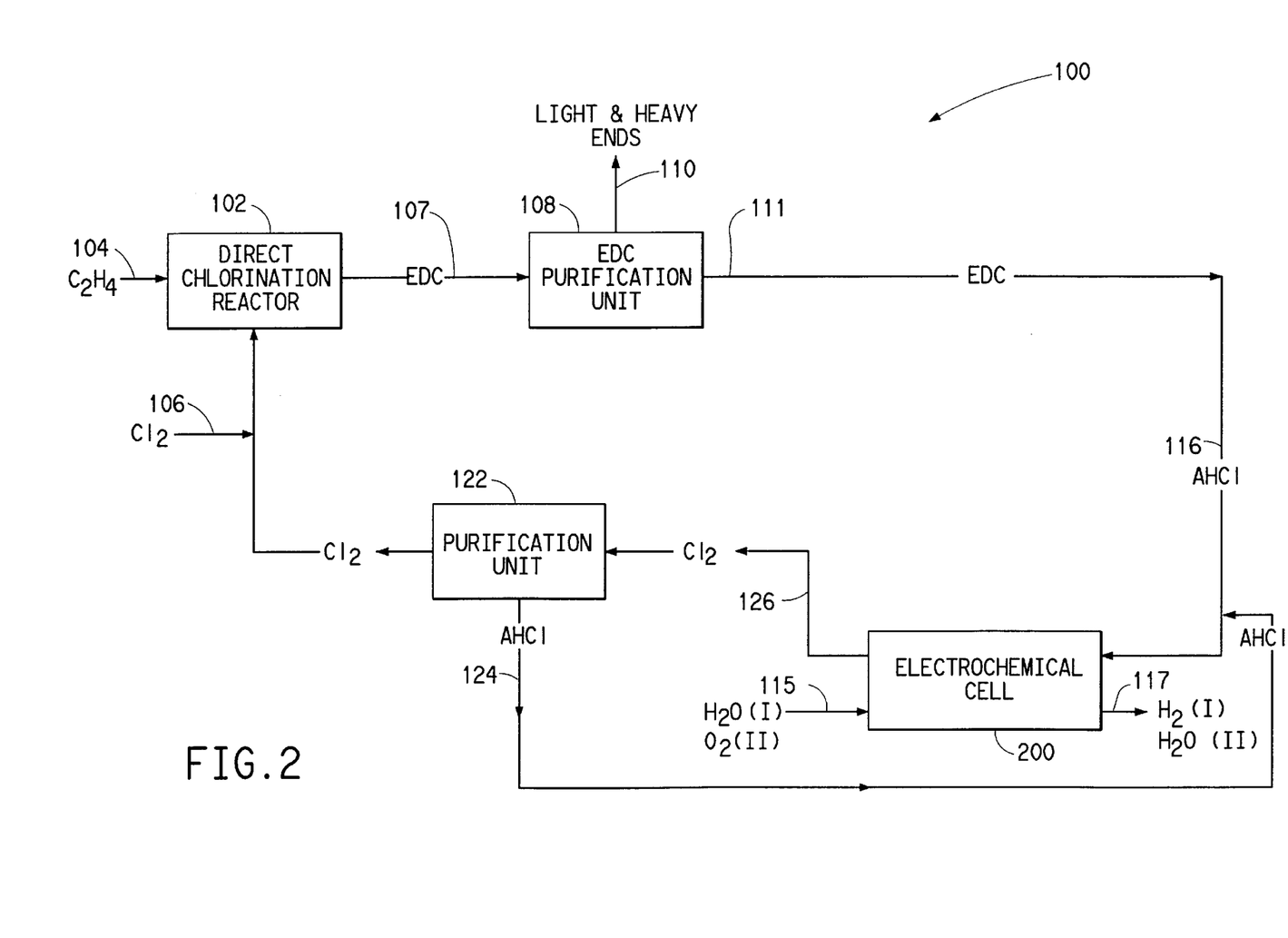
FIG. 2 is a block flow diagram showing a system for producing ethylene dichloride according to the present invention.

System 100 includes a direct chlorination reactor as shown at 102 in FIG. 2. Direct chlorination of ethylene to ethylene dichloride is conducted by mixing ethylene and chlorine in direct chlorination reactor 102. A first inlet supply line 104 as shown in FIG. 2 supplies ethylene ($C_2H_4$) to the direct chlorination reactor. A second inlet supply line 106 supplies liquid dry chlorine ($Cl_2$) to the direct chlorination reactor. The ethylene and the chlorine react in the reactor to produce ethylene dichloride. The equation for this direct chlorination reaction is given by:

$$C_2H_4 + Cl_2 \rightarrow C_2H_4Cl_2 \tag{1}$$

Ferric chloride is a highly selective and efficient catalyst for this reaction and can be used with the present invention, although other catalysts may be used. It should be noted that the feeding of the ethylene and the chlorine may be simultaneous, or may be slightly spaced apart in time, as long as the conditions in the reactor are proper for the direct chlorination reaction to occur.

By-products contained in EDC from the direct chlorination reaction and the ethylene dichloride pyrolysis as described above must be removed. The ethylene dichloride used for pyrolysis to vinyl chloride must be of high purity because the pyrolysis of ethylene dichloride is exceedingly susceptible to inhibition and fouling by trace quantities of impurities. It must also be dry (no separate water phase and very little total dissolved water) to prevent excessive corrosion downstream of the pyrolysis unit. Therefore, the system of the present invention may also include an ethylene dichloride (EDC) purification unit. Such an EDC purification unit is shown at 108 in FIG. 2. The EDC is delivered to the EDC purification unit through a line 107. The EDC purification unit purifies the ethylene dichloride. Light and heavy ends are a by-product of this purification. These light and heavy ends are released through a line 110 as shown in FIG. 2. The purified EDC is sent through a line 111 for further processing, such as making VCM. Since the EDC produced by the present invention is much cleaner than that produced by the oxychlorination process of the prior art, the EDC purification unit of the present invention is much smaller than that of the oxychlorination process, thus reducing capital and operating costs.

Figure 3:
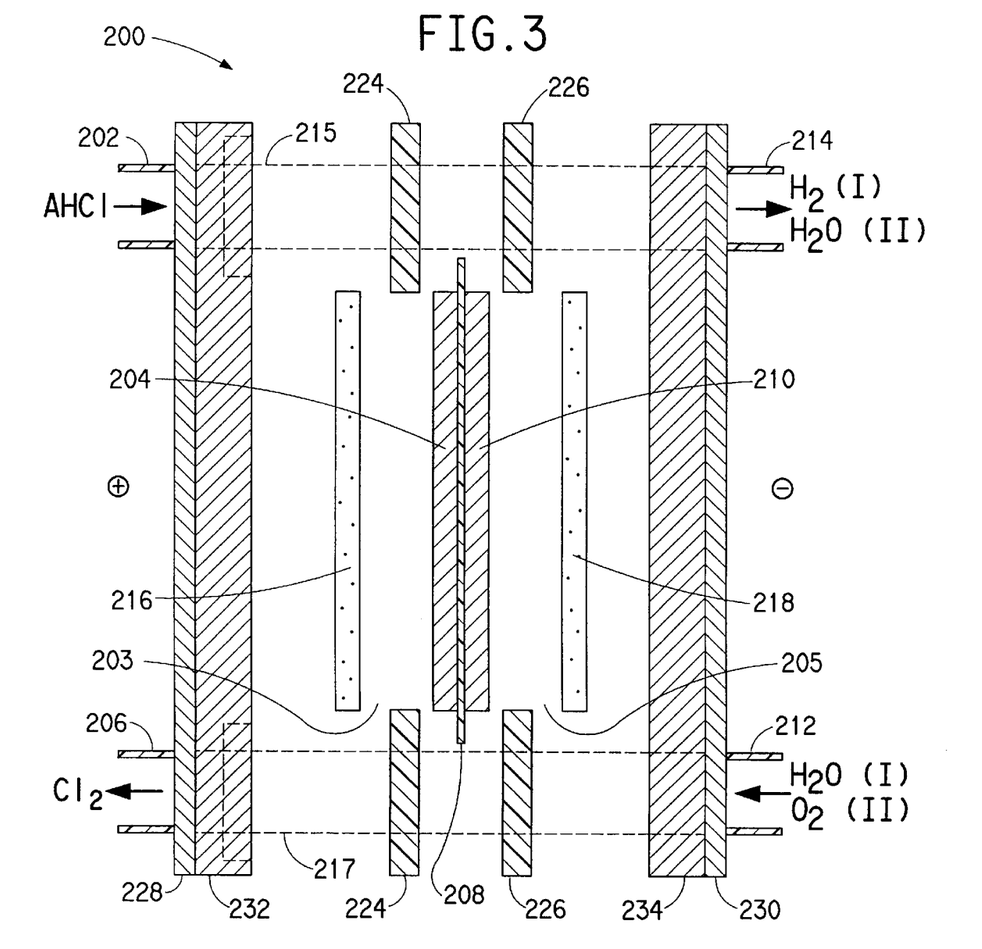
FIG. 3 is a schematic diagram showing the details of an electrochemical cell for producing chlorine gas from anhydrous hydrogen chloride used in the system of FIG. 3.
Figure 3A:
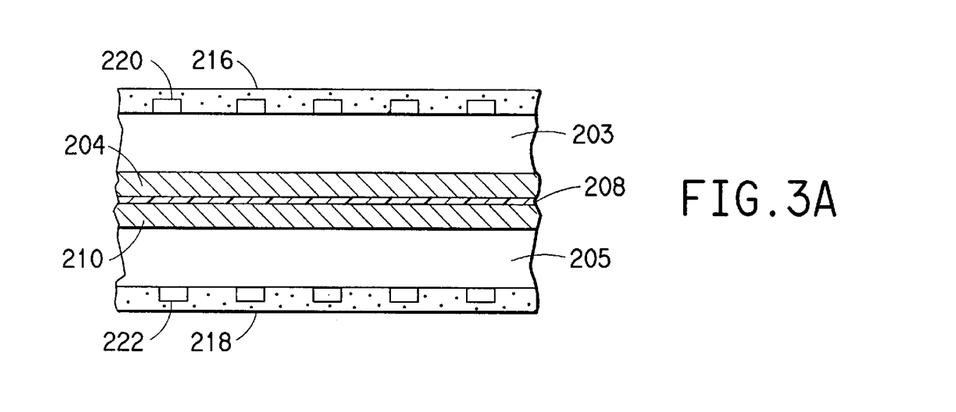
FIG. 3A is a cut-away, top cross-sectional view of the anode and cathode mass flow fields as shown in FIG. 3.

Essentially anhydrous hydrogen chloride, which is the by-product of an unrelated process, is sent via a line 116 as shown in FIG. 2 to an electrochemical cell which directly produces essentially dry chlorine gas. Such a cell is shown at 200 in FIGS. 2 and 3. The electrochemical cell of the present invention includes means for oxidizing the anhydrous hydrogen chloride to produce chlorine gas and protons. The oxidizing means comprises an electrode, or more specifically, an anode 204 as shown in FIGS. 3 and 3A. The oxidizing means oxidizes the anhydrous hydrogen chloride, which is molecular in form, to essentially dry chlorine gas and protons. This reaction is given by the equation:

$$2HCl(g) \xrightarrow{\text{Electrical Energy}} 2H^+ + Cl_2(g) + 2e^- \tag{2}$$

The electrochemical cell of the present invention also comprises an anode chamber disposed adjacent the oxidizing means. An anode chamber is shown at 203 in FIGS. 3 and 3A disposed adjacent, meaning next to or near, the oxidizing means, or anode. The electrochemical cell of the present invention comprises anode-side inlet means disposed in fluid communication with the anode chamber for introducing the anhydrous hydrogen chloride to the oxidizing means. The inlet means comprises an anode-side inlet 202 as shown in FIG. 3. Anhydrous hydrogen chloride, which is a gas, is designated by AHCl in FIGS. 2–4. The electrochemical cell of the present invention also comprises anode-side outlet means also disposed in fluid communication with the anode chamber for discharging the chlorine gas. The anode-side outlet means comprises an anode-side outlet 206 as shown in FIG. 3. A portion of the anhydrous hydrogen chloride may be unreacted, and this unreacted portion leaves the electrochemical cell through the anode-side outlet, along with the essentially dry chlorine gas. Since anhydrous HCl, which is corrosive, is carried through the anode-side inlet, and chlorine gas is carried through the outlet, the inlet and the outlet may be lined with a copolymer of tetrafluoroethylene with perfluoro(alkyl)-vinyl ether, sold under the trademark TEFLON® PFA (hereinafter referred to as by E. I. du Pont de Nemours and Company of Wilmington, Del. (hereinafter referred to as "DuPont").

The electrochemical cell of the present invention also comprises cation-transporting means for transporting the protons therethrough, wherein the 10 oxidizing means is disposed in contact with one side of the cation-transporting means. Preferably, the cation-transporting means is a cation-transporting membrane 208, where the anode is disposed in contact with one side of the membrane as shown in FIGS. 3 and 3A. More specifically, membrane 208 may be a proton-conducting membrane. In the present invention, the membrane acts as the electrolyte. The membrane may be a commercial cationic membrane made of a fluoro- or perfluoropolymer, preferably a copolymer of two or more fluoro or perfluoromonomers, at least one of which has pendant sulfonic acid groups. The presence of carboxylic groups is not desirable, because those groups tend to decrease the conductivity of the membrane when they are protonated. Various suitable resin materials are available commercially or can be made according to the patent literature. They include fluorinated polymers with side chains of the type —$CF_2CFRSO_3H$ and —$OCF_2CF_2SO_3H$, where R is an F, Cl, $CF_2Cl$, or a $C_1$ to $C_{10}$ perfluoroalkyl radical. The membrane resin may be, for example, a copolymer of tetrafluoroethylene with $CF_2$=$CFOCF_2CF(CF_3)OCF_2CF_2SO_3H$. Sometimes those resins may be in the form that has pendant —$SO_2F$ groups, rather than —$SO_3H$ groups. The sulfonyl fluoride groups can be hydrolyzed with potassium hydroxide to —$SO_3K$ groups, which then are exchanged with an acid to —$SO_3H$ groups. Suitable perfluorinated cationic membranes, which are made of hydrated copolymers of polytetrafluoroethylene and poly-sulfonyl fluoride vinyl ether-containing pendant sulfonic acid groups, are offered DuPont under the trademark "NAFION®" (hereinafter referred to as NAFION®). In particular, NAFION® membranes containing pendant sulfonic acid groups include NAFION® 115, NAFION® 117, NAFION® 324 and NAFION® 417. The first and second types of NAFION® are unsupported and have an equivalent weight of 1100 g., equivalent weight being defined as the amount of resin required to neutralize one liter of a 1M sodium hydroxide solution. NAFION® 324 and NAFION® 417 are both supported on a fluorocarbon fabric, the equivalent weight of NAFION® 417 also being 1100 g. NAFION® 324 has a two-layer structure, a 125 μm-thick membrane having an equivalent weight of 1100 g., and a 25 μm-thick membrane having an equivalent weight of 1500 g. NAFION® 115 in particular may be used with the electrochemical cell of the present invention.

Although the present invention describes the use of a solid polymer electrolyte membrane, it is well within the scope of the invention to use other cation-transporting membranes which are not polymeric. For example, proton-conducting ceramics such as beta-alumina may be used. Beta-alumina is a class of nonstoichiometric crystalline compounds having the general structure $Na_2O_x \cdot Al_2O_3$, in which x ranges from 500 (β"-alumina) to 11 (β-alumina). This material and a number of solid electrolytes which are useful for the invention are described in the *Fuel Cell Handbook*, A. J. Appleby and F. R. Foulkes, Van Nostrand Reinhold, N.Y., 1989, pages 308–312. Additional useful solid state proton conductors, especially the cerates of strontium and barium, such as strontium ytterbiate cerate ($SrCe_{0.95}Yb_{0.05}O_{3-\alpha}$) and barium neodymiate cerate ($BaCe_{0.9}Nd_{0.01}O_{3-\alpha}$) are described in a final report, DOE/MC/24218-2957, Jewulski, Osif and Remick, prepared for the U.S. Department of Energy, Office of Fossil Energy, Morgantown Energy Technology Center by Institute of Gas Technology, Chicago, Ill., December, 1990.

The electrochemical cell of the present invention also comprises means for reducing the transported protons, where the reducing means is disposed in contact with the other side of the cation-transporting means. The reducing means comprises an electrode, or more specifically, a cathode 210, where cathode 210 is disposed in contact with the other side (as opposed to the side which is in contact with the anode) of membrane 208 as illustrated in FIGS. 3 and 3A.

The electrochemical cell of the present invention also includes a cathode chamber disposed adjacent the reducing means. A cathode chamber is shown at 205 in FIGS. 3 and 3A disposed adjacent to, meaning next to or near, the reducing means, or cathode. The electrochemical cell of the present invention also comprises cathode-side inlet means disposed in fluid communication with the cathode chamber for introducing a fluid to the other side of the cation-transporting means. The cathode-side inlet means comprises a cathode-side inlet 212 as shown in FIG. 3. The cathode-side inlet means is connected to a line, such as line 115 as shown in FIG. 2. The cathode-side inlet introduces a fluid, such as water, to the cathode-side of the membrane in the first embodiment, or an oxygen-containing gas, such as oxygen gas, to the cathode and then to the cathode-side of the membrane in the second embodiment, as will be explained below. The electrochemical cell of the present invention also comprises cathode-side outlet means also disposed in fluid communication with the cathode chamber. The cathode-side outlet means comprises a cathode-side outlet 214 as shown in FIG. 3. The cathode-side outlet is connected to a line, such as line 117 as shown in FIG. 2. Since some chloride ions pass through the membrane and, consequently, HCl is present on the cathode-side of the cell, the cathode inlet and the outlet may also be lined with PFA. A passage 215 as shown in FIG. 3 is formed between the anode-side inlet and the cathode-side outlet, and a similar passage 217 is shown formed between the cathode-side inlet and the anode-side outlet. These passages carry the reactants into and the products out of the cell through the anode and cathode-side inlets, and the anode and cathode-side outlets, as will be further explained below.

The anode and the cathode comprise an electrochemically active material. The electrochemically active material may comprise any type of catalytic or metallic material or metallic oxide, as long as the material can support charge transfer. Preferably, the electrochemically active material may comprise a catalyst material such as platinum, ruthenium, osmium, rhenium, rhodium, iridium, palladium, gold, titanium, tin or zirconium and the oxides, alloys or mixtures thereof. Other catalyst materials suitable for use with the present invention may include, but are not limited to, transition metal macro cycles in monomeric and polymeric forms and transition metal oxides, including perovskites and pyrochores.

The anode and the cathode may be porous, gas-diffusion electrodes. Gas diffusion electrodes provide the advantage of high specific surface area, as known to one skilled in the art. A particular type of gas diffusion electrode, known as an ELAT, may be used as the anode and the cathode. An ELAT comprises a support structure, as well as the electrochemically active material. In one preferred embodiment, an ELAT comprising a support structure of carbon cloth and electrochemically active material comprising ruthenium oxide, commercially available from E-TEK, of Natick, Mass., may be used. Alternatively, an ELAT may be used which comprises a catalyst material mixed with carbon and particles of polytetrafluoroethylene, or PTFE, a tetrafluoropolymer resin which is sold under the trademark "TEFLON®" (hereinafter referred to as "PTFE"), commercially available from DuPont. The catalyst material, carbon particles and PTFE are then sintered on a carbon cloth substrate, which is treated with a NAFION® solution. This ELAT is held mechanically against the membrane of the cell.

Alternative arrangements of the electrochemically active material may be used for the anode and cathode of the present invention. The electrochemically active material may be disposed adjacent, meaning at or under, the surface of the cation-transporting membrane. For instance, the electrochemically active material may be deposited into the membrane, as shown in U.S. Pat. No. 4,959,132 to Fedkiw. A thin film of the electrochemically active material may be applied directly to the membrane. Alternatively, the electrochemically active material may be hot-pressed to the membrane, as shown in A. J. Appleby and E. B. Yeager, Energy, Vol. 11, 137 (1986).

If the electrodes are hot-pressed into the membrane, they have the advantage of having good contact between the catalyst and the membrane. In a hot-pressed electrode, the electrochemically active material may comprise a catalyst material on a support material. The support material may comprise particles of carbon and particles of PTFE. The electrochemically active material may be bonded by virtue of the PTFE to a support structure of carbon cloth or paper or graphite paper and hot-pressed to the cation-transporting membrane. The hydrophobic nature of PTFE does not allow a film of water to form at the anode. A water barrier in the electrode would hamper the diffusion of HCl to the reaction sites.

The loadings of electrochemically active material may vary based on the method of application to the membrane. Hot-pressed, gas-diffusion electrodes typically have loadings of 0.10 to 0.50 mg/cm$^2$. Lower loadings are possible with other available methods of deposition, such as distributing them as thin films from inks onto the membranes, to form a catalyst-coated membrane, as described in Wilson and Gottesfeld, "High Performance Catalyzed Membranes of Ultra-low Pt Loadings for Polymer Electrolyte Fuel Cells", Los Alamos National Laboratory, J. Electrochem. Soc., Vol. 139, No. 2 L28–30, 1992, where the inks contain solubilized NAFION® to enhance 10 the catalyst-ionomer surface contact and to act as a binder to the NAFION® perfluorinated membrane sheet.

With such a system, loadings as low as 0.017 mg active material per cm$^2$ have been achieved.

In a preferred embodiment, a thin film of the electrochemically active material is be applied directly to the membrane to form a catalyst-coated membrane. In this preferred embodiment, the membrane is typically formed from a polymer as described above in its sulfonyl fluoride form, since it is thermoplastic in this form, and conventional techniques for making films from thermoplastic polymer can be used. The sulfonyl fluoride, or $SO_2F$, form means that the side chain, before the membrane is hydrolyzed, has the formula $[—OCF_2CF(CF_3)]n\text{-}OCF_2CF_2SO_2F$. Alternately, the polymer may be in another thermoplastic form such as by having $—SO_2X$ groups where X is $CH_3$, $CO_2$, or a quaternary amine. Solution film casting techniques using suitable solvents for the particular polymer can also be used if desired.

A film of the polymer in sulfonyl fluoride form can be converted to the sulfonate form (sometimes referred to as ionic form) by hydrolysis using methods known in the art. For example, the membrane may be hydrolyzed to convert it to the sodium sulfonate form by immersing it in 25% by weight NaOH for about 16 hours at a temperature of about 90° C. followed by rinsing the film twice in deionized 90° C. water using about 30 to about 60 minutes per rinse. Another possible method employs an aqueous solution of 6–20% of an alkali metal hydroxide and 5–40% polar organic solvent such as dimethyl sulfoxide with a contact time of at least 5 minutes at 50°–100° C. followed by rinsing for 10 minutes. After hydrolyzing, the membrane can be converted if desired to another ionic form by contacting the membrane in a bath containing a 1% salt solution containing the desired cation or, to the acid form, by contacting with an acid and rinsing. The membrane used in the membrane-electrode assembly of the present invention is usually in the sulfonic acid form.

The thickness of the membrane can be varied as desired. Typically, the thickness of the membrane is generally less than about 250 $\mu$m, preferably in the range of about 25 $\mu$m to about 150 $\mu$m.

The electrochemically active material is conventionally incorporated in a coating formulation, or "ink", which is applied to the membrane. The electrochemically active material in the form of particles having a particle diameter in the range of 0.1 micron ($\mu$) to 10$\mu$. The coating formulation, and consequently the anode and the cathode after the catalyst coated membrane is formed, also comprises a binder polymer for binding the particles of the electrochemically active material together. The particles of electrochemically active material, when coated with the binder polymer, have a tendency to agglomerate. By grinding the particles to a particularly small size, a better particle distribution may be obtained. Thus, the coating formulation is ground so that the particles have an average diameter of less than 5$\mu$, and in many cases, preferably less than 2$\mu$. This small particle size is accomplished by ball milling or grinding with an Elger mini mill, which latter technique can produce particles of 1$\mu$ or less.

The binder polymer is dissolved in a solvent. The binder polymer may be the same polymer as that used for the membrane, as described herein, but it need not be. The binder polymer may be a variety of polymers, such as polytetrafluoroethylene (PTFE). In a preferred embodiment, the binder polymer is a perfluorinated sulfonic acid polymer, and the side chain of the binder polymer, before hydrolyzation of the binder polymer, is represented by the formula $[\text{-}OCF_2CF(CF_3)]n\text{-}OCF_2CF_2SO_2F$ (i.e., the $SO_2F$, or sulfonyl fluoride form). The side chain, after hydrolyzation, is represented by the formula $[—OCF_2CF(CF_3)]—OCF_2CF_2SO_3H$ (i.e., the $SO_3H$, sulfonic acid, or acid form). When the binder polymer is in the sulfonyl fluoride form, the solvent can be a variety of solvents, such as FLUORINERT FC-40, commercially available from 3M of St. Paul, Minn., which is a mixture of perfluoro(methyl-di-n-butyl)amine and perfluoro(tri-n-butylamine). In this embodiment, a copolymer polymerized from tetrafluoroethylene and a vinyl ether which is represented by the formula $CF_2=CF-O-CF_2CF(CF_3)-O-CF_2CF_2SO_2F$ has been found to be a suitable binder polymer. In addition, ruthenium dioxide has been found to be a suitable catalyst. The sulfonyl fluoride form has been found to be compatible with FC-40 and to give a uniform coating of the ruthenium dioxide catalyst on the membrane.

The viscosity of the ink can be controlled by (i) selecting particle sizes, (ii) controlling the composition of the particles of electrochemically active material and binder, or (iii) adjusting the solvent content (if present). The particles of electrochemically active material are preferably uniformly dispersed in the polymer to assure that a uniform and controlled depth of the catalyst layer is maintained, preferably at a high volume density with the particles of electrochemically active material being in contact with adjacent particles to form a low resistance conductive path through the catalyst layer. The ratio of the particles of electrochemically active material to the binder polymer may be in the range of about 0.5:1 to about 8:1, and in particular in the range of about 1:1 to about 5:1. The catalyst layer formed on the membrane should be porous so that it is readily permeable to the gases/liquids which are consumed and produced in cell. The average pore diameter is preferably in the range of 0.01 to 50 $\mu$m, most preferably 0.1 to 30 $\mu$m. The porosity is generally in a range of 10 to 99%, preferably 10 to 60%.

The area of the membrane to be coated with the ink may be the entire area or only a select portion of the surface of the membrane. If desired, the coatings are built up to the thickness desired by repetitive application. Areas upon the surface of the membrane which require no particles of electrochemically active material can be masked, or other means can be taken to prevent the deposition of the particles of electrochemically active material upon such areas. The desired loading of particles of electrochemically active material upon the membrane can be predetermined, and the specific amount of particles of electrochemically active material can be deposited upon the surface of the membrane so that no excess electrochemically active material is applied. In a preferred embodiment, the ink is deposited on the surface of the membrane by spraying. However, it should be noted that the catalyst ink may be deposited upon the surface of the membrane by any suitable technique, including spreading it with a knife or blade, brushing, pouring, metering bars and the like. Alternatively, the electrochemically active material may be applied to the membrane by using a screen printing process, as known in the art. An alternative to printing the electrochemically active material directly onto the membrane is the decal process, also known in the art, where the catalyst ink is coated, painted, sprayed or screen printed onto a substrate and the solvent is removed. The resulting decal is then subsequently transferred from the substrate to the membrane surface and bonded, typically by the application of heat and pressure.

After depositing the catalyst layer of electrochemically active material, it is preferable to fix the ink on the surface of the membrane so that a strongly bonded catalyst layer and the cation-transporting membrane can be obtained. The ink may be fixed upon the surface of the membrane by any one or a combination of pressure, heat, adhesive, binder, solvent, electrostatic, and the like. A preferred method for fixing the ink upon the surface of the membrane employs pressure, heat or by a combination of pressure and heat. The catalyst layer is preferably pressed onto the surface of the membrane at 100° C. to 300° C., most preferably 150° C. to 280° C., under a pressure of 510 to 51,000 kPa (5 to 500 ATM), most preferably 1,015 to 10,500 kPa (10 to 100 ATM).

If a catalyst-coated membrane as described above is used, the electrochemical cell must include a gas diffusion layer (not shown) disposed in contact with the anode and the cathode, respectively, (or at least in contact with the anode), on the side of the anode or cathode opposite the side which is in contact with the membrane. The gas diffusion layer provides a porous structure that allows the anhydrous hydrogen chloride to diffuse through to the layer of electrochemically active material of the catalyst-coated membrane. In addition, both the anode gas diffusion layer and the cathode gas diffusion layer distribute current over the electrochemically active material, or area, of the catalyst-coated membrane. The diffusion layers are preferably made of graphite paper, and are typically 15–20 mil thick.

When using any type of membrane and electrodes with the present invention, the membrane must be kept hydrated in order to increase the efficiency of proton transport through the membrane. This keeps the conductivity of the membrane high. In the first embodiment, which has a hydrogen-producing cathode, the hydration of the membrane is obtained by keeping liquid water in contact with the cathode-side of the membrane, as will be explained below. For example, when using gas diffusion electrodes, liquid water is delivered to the cathode, and the liquid water passes through the gas-diffusion electrode and contacts the membrane. When using a catalyst-coated membrane, liquid water is delivered to the membrane itself, since the cathode is a thin layer of electrochemically active material applied directly to the membrane.

In particular, in the first embodiment, water is added to the electrochemical cell through cathode-side inlet 212. The protons (2H+ in eq. (2) above) which are produced by the oxidation of the anhydrous hydrogen chloride are transported through the membrane and reduced at the cathode to form hydrogen gas, as given by equation (3) below.

$$2H^+ + 2e^- \xrightarrow{\text{Electrical Energy}} H_2(g) \qquad (3)$$

This hydrogen gas is evolved at the interface between the cathode and the membrane. The hydrogen gas, which is shown as $H_2(I)$ for the first embodiment in FIGS. 2 and 3, exits the cell through the cathode-side outlet and through a line 115 as shown in FIG. 1. The hydrogen gas may have some HCl therein due to chloride ion migration. The hydrogen gas may be used for other purposes, such as a fuel.

In the second embodiment, membrane hydration is accomplished by the production of water and by the water introduced in a humidified oxygen-feed or air-feed stream. In particular, in the second embodiment, an oxygen-containing gas, such as oxygen, air or oxygen-enriched air (i.e., greater than 21 mol % oxygen in nitrogen) is introduced through cathode-side inlet 112. Although air is cheaper to use, cell performance is enhanced when enriched air or oxygen is used. This oxygen-containing gas should be humidified to aid in the control of moisture in the membrane, for purposes to be explained below. The oxygen gas ($O_2$) and the transported protons are reduced at the cathode to water, as expressed by the equation:

$$\tfrac{1}{2}O_2(g)+2e^-+2H^+\rightarrow H_2O(g) \qquad (4)$$

The water formed, as illustrated by $H_2O(II)$ in FIGS. 2 and 3, denoting the second embodiment, exits via the cathode-side outlet, along with any unreacted nitrogen and oxygen gas. The water may have some HCl therein due to chloride ion migration, as in the first embodiment.

In the second embodiment, the cathode reaction is the formation of water. This cathode reaction has the advantage of more favorable thermodynamics relative to $H_2$ production at the cathode in the first embodiment. This is because the overall reaction in this embodiment, which is expressed by the following equation:

$$2HCl(g) + 1/2O_2(g) \xrightarrow{\text{Electrical Energy}} H_2O(g) + 2Cl^- \quad (5)$$

involves a smaller free-energy change than the free-energy change for the overall reaction in the first embodiment, which is expressed by the following equation:

$$2HCl(g) \xrightarrow{\text{Electrical Energy}} H_2(g) + 2Cl^- \quad (6)$$

Thus, the amount of voltage or energy required as input to the cell is reduced in this second embodiment.

Returning again to the description of FIG. 2, the electrochemical cell of the present invention further comprises an anode flow field 216 disposed in contact with the anode and a cathode flow field 218 disposed in contact with the cathode as shown in FIGS. 3 and 3A. The flow fields are electrically conductive, and act as both mass and current flow fields. Preferably, the anode and the cathode flow fields comprise porous graphite paper. Such flow fields are commercially available from Spectracorp, of Lawrence, Mass. However, the flow fields may be made of any material and in any manner known to one skilled in the art. For example, the flow fields may alternatively be made of a porous carbon in the form of a foam, cloth or matte. For the purpose of acting as mass flow fields, the anode mass flow field includes a plurality of anode flow channels 220, and the cathode mass flow field includes a plurality of cathode flow channels 222 as shown in FIG. 3A, which is a cut-away, top cross-sectional view showing only the flow fields of FIG. 3. The anode flow fields and the anode flow channels, get reactants, such as anhydrous HCl in the first and second embodiments, to the anode and products, such as dry chlorine gas, from the anode. The cathode flow field and the cathode flow channels get catholyte, such as liquid water in the first embodiment, to the membrane, or an oxygen-containing gas to the cathode in the second embodiment, and products, such as hydrogen gas in the first embodiment, or liquid water in the second embodiment, from the cathode.

The electrochemical cell of the present invention may also comprise an anode-side gasket 224 and a cathode-side gasket 226 as shown in FIG. 3. Gaskets 224 and 226 form a seal between the interior and the exterior of the electrochemical cell. Preferably, the anode-side gas is made of a fluoroelastomer, sold under the trademark VITON® (hereinafter referred to as VITON®) by DuPont Dow Elastomers L.L.C. of Wilmington, Del. The cathode-side gasket may be made of the terpolymer ethylene/propylene/diene (EPDM), sold under the trademark NORDEL® by DuPont, or it may be made of VITON®.

The electrochemical cell of the present invention also comprises an anode current bus 228 and a cathode current bus 230 as shown in FIG. 3. The current buses conduct current to and from a voltage source (not shown). Specifically, anode current bus 228 is connected to the positive terminal of a voltage source, and cathode current bus 230 is connected to the negative terminal of the voltage source, so that when voltage is applied to the cell, current flows through all of the cell components to the right of current bus 228 as shown in FIG. 3, including current bus 230, from which it returns to the voltage source. The current buses are made of a conductor material, such as copper.

The electrochemical cell of the present invention may further comprise an anode current distributor 232 as shown in FIG. 3. The anode current distributor collects current from the anode current bus and distributes it to the anode by electronic conduction. The anode current distributor may comprise a fluoropolymer which has been loaded with a conductive material. In one embodiment, the anode current distributor may be made from polyvinylidene fluoride, sold under the trademark KYNAR® (hereinafter referred to as "KYNAR®") by Elf Atochem North America, Inc. Fluoropolymers, and graphite.

The electrochemical cell of the present invention may further comprise a cathode current distributor 234 as shown in FIG. 3. The cathode current distributor collects current from the cathode and for distributing current to the cathode bus by electronic conduction. The cathode distributor also provides a barrier between the cathode current bus and the cathode and the hydrogen chloride. This is desirable because there is some migration of hydrogen chloride through the membrane. Like the anode current distributor, the cathode current distributor may comprise a fluoropolymer, such as KYNAR®, which has been loaded with a conductive material, such as graphite.

The electrochemical cell of the present invention also includes an anode-side stainless steel backer plate (not shown), disposed on the outside of the cell next to the anode current distributor, and a cathode-side stainless steel backer plate (also not shown), disposed on the outside of the cell next to the cathode current distributor. These steel backer plates have bolts extending therethrough to hold the components of the electrochemical cell together and add mechanical stability thereto.

When more than one anode-cathode pair is used, such as in manufacturing, a bipolar arrangement, as familiar to one skilled in the art, is preferred. The electrochemical cell of the present invention may be used in a bipolar stack. To create such a bi-polar stack, anode current distributor 232 and every element to the right of the anode current distributor as shown in FIG. 3, up to and including cathode current distributor 234, are repeated along the length of the cell, and current buses are placed on the outside of the stack.

Returning again to the description of FIG. 2, the system of the present invention further comprises a purification unit 122, which liquefies and purifies the essentially dry chlorine gas. Liquid dry chlorine exits the purifier. As noted above, a portion of the anhydrous hydrogen chloride may be unreacted. This unreacted portion exits electrochemical cell 200, along with the essentially dry chlorine gas, and is sent to purification unit 122. The purification unit separates out the unreacted anhydrous hydrogen chloride (AHCl as shown in FIG. 2) from the liquid dry chlorine and returns it through line 124 to line 116, which is connected to the anode-side inlet as shown in FIG. 2.

The system of the present invention further comprises a recycle line connected to the electrochemical cell outlet means at one end thereof and to the second inlet supply line at the other end thereof for recycling the liquid dry chlorine to the direct chlorination reactor. A recycle line, shown at 126 in FIG. 2 joins second inlet feed line 106 to supply fresh liquid dry chlorine to the direct chlorination reactor.

Figure 4:
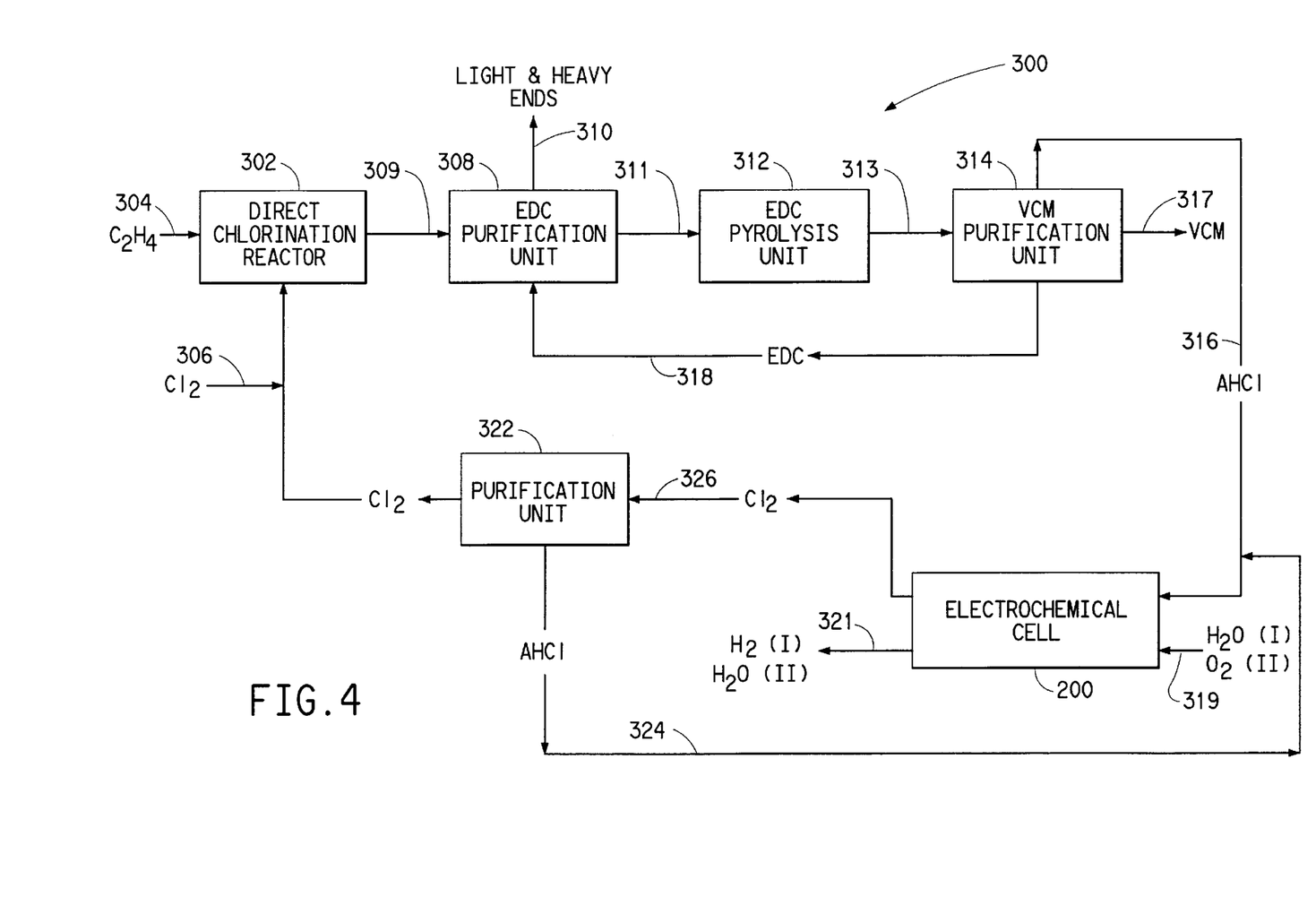
FIG. 4 is a block flow diagram showing a system for producing ethylene-based vinyl chloride according to the present invention.

Further in accordance with the present invention, there is provided a system for producing vinyl chloride monomer from chlorine gas produced by the electrochemical conversion of anhydrous hydrogen chloride. Such a system is shown generally at 300 in FIG. 4. System 300 includes a direct chlorination reactor as shown at 302 in FIG. 4. Direct chlorination of ethylene to ethylene dichloride is conducted by mixing ethylene and chlorine in direct chlorination reactor 302. A first inlet supply line 304 as shown in FIG. 4 supplies ethylene ($C_2H_4$) to the direct chlorination reactor. A second inlet supply line 306 supplies liquid dry chlorine ($Cl_2$) to the direct chlorination reactor. The ethylene and the chlorine react in the reactor to produce ethylene dichloride. The equation for this reaction is given by equation (1) above. As noted above, ferric chloride can be used as a catalyst with the present invention, although other catalysts may be used. It should be noted that the feeding of the ethylene and the chlorine may be simultaneous, or may be slightly spaced apart in time, as long as the conditions in the reactor are proper for the direct chlorination reaction to occur.

By-products contained in EDC from the direct chlorination reaction and the ethylene dichloride pyrolysis as described above must be removed. The ethylene dichloride used for pyrolysis to vinyl chloride must be of high purity because the pyrolysis of ethylene dichloride is exceedingly susceptible to inhibition and fouling by trace quantities of impurities. It must also be dry (no separate water phase and very little total dissolved water) to prevent excessive corrosion downstream of the pyrolysis unit. Therefore, the system of the present invention may also include an ethylene dichloride purification unit connected to the direct chlorination unit for purifying the ethylene dichloride. Such an EDC purification unit is shown at 308 in FIG. 4. The EDC is brought to the EDC purification unit from the direct chlorination reactor through a line 309. The EDC purification unit purifies the ethylene dichloride. Light and heavy ends are a by-product of this purification. These light and heavy ends are released through a line 310 as shown in FIG. 4. As noted above for the EDC system, the EDC purification unit of the present invention is much smaller than that of the oxychlorination process, thus reducing capital and operating costs.

The system of the present invention also includes a pyrolysis unit for pyrolyzing the ethylene dichloride to produce vinyl chloride monomer. Such a unit is shown at 312 in FIG. 4. The purified EDC is brought to the pyrolysis unit through a line 311. The pyrolysis unit pyrolyzes the ethylene dichloride from line 311 to produce vinyl chloride monomer, as well anhydrous hydrogen chloride, i.e., hydrogen chloride in molecular form (AHCl as shown in FIG. 4). This reaction is given by the following equation.

$$2ClCH_2CH_2Cl \rightarrow 2CH_2\!=\!CHCl + 2\ AHCl \qquad (7)$$

The system of the present invention also includes a vinyl chloride monomer purification unit connected to the ethylene dichloride purification unit for purifying the vinyl chloride monomer and for separating the vinyl chloride monomer from the anhydrous hydrogen chloride. Such a unit is shown at 314 in FIG. 4. The VCM is brought to the VCM purification unit from the EDC pyrolysis unit through a line 313. VCM purification unit 314 purifies the VCM and separates the VCM from the anhydrous hydrogen chloride so that the VCM exits the VCM purification unit through a line 317, and the anhydrous hydrogen chloride exits the VCM purification unit through a line 316 as shown in FIG. 4.

In the production of vinyl chloride monomer in the present invention, a portion of the ethylene dichloride may be unreacted in pyrolysis unit 312. Therefore, the system of the present invention also includes a recycle line connected to the vinyl chloride monomer purification unit for recycling the unreacted ethylene dichloride to the ethylene dichloride purification unit. This recycle line is shown at 318 in FIG. 4. In the prior art as shown in FIG. 1, the unreacted portion is normally mixed with fresh ethylene dichloride supplied from the direct chlorination unit and the OHC reactor in the ethylene dichloride purification unit. However, since the ethylene dichloride produced according to the present invention is much cleaner than that produced by the OHC process of the prior art, the unreacted ethylene dichloride may be recycled back to the ethylene dichloride purification unit through recycle line 318.

The anhydrous hydrogen chloride is sent through line 318 to an electrochemical cell, which is shown generally at 200 in FIGS. 3 and 4 and in detail in FIG. 3. The details of the cell are as described above. The anhydrous hydrogen chloride enters the cell through anode-side inlet 202 as shown in FIG. 3. Either water in the first embodiment or an oxygen-containing gas in the second embodiment, as explained above, enters the cell through a line 319 as shown in FIG. 4 and through cathode-side inlet 212 as shown in FIG. 3. Hydrogen in the first embodiment, designated by $H_2(I)$ in FIGS. 3 and 4, or water in the second embodiment, designated by $H_2O(II)$ in FIGS. 3 and 4, leaves the cell through cathode-side outlet 214 which is shown in FIG. 3 and through a line 321 as shown in FIG. 4. Essentially dry chlorine gas ($Cl_2$ as shown in FIG. 4) exits the cell through anode-side outlet 206 which is shown in FIG. 3.

The system of the present invention further includes a purification unit disposed in communication with the outlet means for purifying and liquefying the essentially dry chlorine gas. Such a purification unit is shown at 322 shown in FIG. 4. The chlorine entering purification unit 322 is dry chlorine gas, whereas the chlorine gas leaving the purification unit is liquid dry chlorine. As noted above, a portion of the anhydrous hydrogen chloride may be unreacted. This unreacted portion exits electrochemical cell 200, along with the essentially dry chlorine gas, and is sent to the purification unit. The purification unit separates out the unreacted anhydrous hydrogen chloride (AHCl as show in FIG. 4) from the liquid dry chlorine and returns it through line 324 to line 316, which is connected to the anode-side inlet as shown in FIG. 4.

The system of the present invention further comprises a recycle line connected to the electrochemical cell outlet means at one end thereof and to the second inlet supply line at the other end thereof for recycling the liquid dry chlorine to the direct chlorination reactor. A recycle line, shown at 326 in FIG. 4 recycles the liquid dry chlorine produced in electrochemical cell 200 to the direct chlorination reactor. Recycle line 326 joins second inlet feed line 306 to supply fresh liquid dry chlorine to the direct chlorination reactor.

Further in accordance with the present invention, there is provided a process for producing ethylene dichloride from chlorine gas produced by the electrochemical conversion of anhydrous hydrogen chloride. The operation of the system of the present invention as described above with respect to FIGS. 2, 3 and 3A will now be described as it relates to the process of the present invention.

The process includes the step of supplying ethylene through a first inlet supply line, such as supply line 104 as shown in FIG. 2, to a direct chlorination reactor, such as reactor 102 as shown in FIG. 2. In addition, the process of the present invention includes the steps of supplying chlorine, that is liquid dry chlorine, through a second inlet supply line, such as line 106 as shown in FIG. 2, to the direct chlorination reactor. The ethylene and the chlorine gas may be supplied to the direct chlorination reactor simultaneously, or at different times. The ethylene reacts with the chlorine in the presence of a catalyst in the direct chlorination reactor to form ethylene dichloride according to equation (1) above. The ethylene dichloride may be sent to an ethylene dichloride purification unit, such as unit 108 as shown in FIG. 2. The light and heavy ends escape from the unit through a line, such as line 110.

In addition, the process includes the step of supplying anhydrous hydrogen chloride, which is in molecular form, to an anode-side inlet of an electrochemical cell, such as anode-side inlet 202 of electrochemical cell 200. The electrochemical cell comprises a cation-transporting membrane, such as membrane 208, an anode disposed in contact with one side of the membrane, such as anode 204 as shown in FIG. 3, and a cathode disposed in contact with the other side of the membrane, such as cathode 210. A voltage is applied to the electrochemical cell so that the anode is at a higher potential than the cathode and so that the molecular essentially anhydrous hydrogen chloride is transported through flow channels, such as channels 220 in anode mass flow field 216 and to the surface of the anode and is oxidized at the anode to produce chlorine gas and protons ($H^+$). The chlorine gas is released from an anode-side outlet of the cell, such as anode-side outlet 206 as shown in FIG. 3.

The process of the present invention further includes the step of recycling the chlorine gas back to the direct chlorination reactor through a recycle line, such as line 126, as shown in FIG. 2. A purification unit, such as unit 122 as shown in FIG. 2, is provided in the recycle line. The chlorine gas is essentially dry when it is released from the anode-side outlet of the cell. Thus, the present invention further includes the step of purifying and liquefying the essentially dry chlorine gas in a purification unit, such as unit 122, to form liquid dry chlorine, and supplying the liquid dry chlorine to the direct chlorination reactor. The liquid dry chlorine is supplied to the direct chlorination reactor through a recycle line, such as line 126 as shown in FIG. 2. In addition, a fresh supply of liquid dry chlorine is supplied to the direct chlorination reactor through a second inlet supply line, such as through line 106 as shown in FIG. 2.

The protons produced in the electrochemical cell are transported through the membrane, which acts as an electrolyte. The transported protons are reduced at the cathode. A cathode current distributor 232 collects current from cathode 210 and distributes it to cathode bus 230. In the first embodiment, in order to maintain hydration of the membrane, water is delivered to the membrane at the cathode-side through a cathode-side inlet, such as inlet 212 as shown in FIG. 3, and through the channels in the cathode mass flow field, such as channels 222 in cathode mass flow field 218 as shown in FIG. 3A to hydrate the membrane and thereby increase the efficiency of proton transport through the membrane. The hydrogen gas which is evolved at the interface between the cathode and the membrane as described above exits via a cathode-side outlet, such as outlet 214 as shown in FIG. 3. In the second embodiment, in order to maintain hydration of the membrane, an oxygen-containing gas, such as oxygen ($O_2(g)$), which is preferably humidified, is introduced through a cathode-side inlet, such as inlet 212, and through the channels formed in the cathode mass flow field, such as channels 222 in flow field 218 as shown in FIG. 3A. Oxygen and the transported protons are reduced at the cathode to form water, as explained above. The water exits via a cathode-side outlet, such as outlet 214 as shown in FIG. 3.

A portion of the anhydrous hydrogen chloride may be unreacted in the electrochemical cell. This unreacted portion exits the electrochemical cell, along with the essentially dry chlorine gas, through an anode-side outlet, such as outlet 202, and is sent to a purification unit, such as unit 122 as shown in FIG. 2. The purification unit separates out the unreacted anhydrous hydrogen chloride. The present invention thus may further include the step of recycling the unreacted anhydrous hydrogen chloride to the anode-side inlet of the electrochemical cell through a recycle line, such as line 124 as shown in FIG. 2.

Further in accordance with the present invention, there is provided a process for producing vinyl chloride monomer from chlorine gas produced by the electrochemical conversion of anhydrous hydrogen chloride. The operation of the system of the present invention as described above with respect to FIGS. 3, 3A and 4 will now be described as it relates to the process of the present invention.

The process includes the steps of supplying ethylene through a first inlet supply line, such as first inlet line 304 as shown in FIG. 4 to a direct chlorination reactor, such as direct chlorination reactor 302 as shown in FIG. 4. In addition, the process includes the step of supplying liquid dry chlorine through a second inlet supply line, such as line 306 as shown in FIG. 4, to the direct chlorination reactor. The ethylene and the chlorine gas may be supplied to the direct chlorination reactor simultaneously, or at different times. The ethylene reacts with the chlorine in the presence of a catalyst in the direct chlorination reactor to form ethylene dichloride according to equation (1) above.

The process of the present invention further includes the step of pyrolyzing the ethylene dichloride to produce vinyl chloride monomer and anhydrous hydrogen chloride. The ethylene dichloride is pyrolyzed in a pyrolysis unit, such as unit 312 as shown in FIG. 4, purifying the ethylene dichloride in an ethylene dichloride purification unit, such as unit 308 as shown in FIG. 4.

The process of the present invention may further include the step of purifying the ethylene dichloride in an ethylene dichloride purification unit, such as unit 308 as shown in FIG. 4, before it is pyrolyzed. The light and heavy ends escape from the unit through a line, such as line 310. The purified ethylene dichloride is sent to a pyrolysis unit, such as unit 312 as shown in FIG. 4.

The process of the present invention may further include the step of purifying the vinyl chloride monomer in a vinyl chloride monomer purification unit, such as in a purification unit 314 as shown in FIG. 4. The purified VCM is sent for further purification, such as through line 317 as shown in FIG. 4.

In the pyrolysis unit, a portion of the ethylene dichloride may be unreacted. The unreacted ethylene dichloride is sent to the vinyl chloride purification unit. In the purification unit, the unreacted EDC is separated from the VCM. Thus, the present invention may further include the step of recycling the unreacted ethylene dichloride from the vinyl chloride monomer purification unit back to the ethylene dichloride purification unit.

In addition, the VCM purification unit separates the unreacted essentially anhydrous hydrogen chloride from the VCM, and sends it to an electrochemical cell, such as electrochemical cell 200 as shown in FIGS. 3 and 4 through a line, such as line 316 as shown in FIG. 4. The electrochemical cell converts anhydrous hydrogen chloride to dry chlorine gas and protons, as described above.

The process of the present invention further includes the step of liquefying and purifying the dry chlorine gas in a purification unit, such as unit 322 as shown in FIG. 4, to form liquid dry chlorine and supplying this liquid dry chlorine to the direct chlorination reactor. The liquid dry chlorine is recycled to the direct chlorination reactor through a recycle line, such as line 326 as shown in FIG. 4. In addition, a fresh supply of liquid dry chlorine is supplied to the direct chlorination reactor through a second inlet supply line, such as through line 306 as shown in FIG. 4.

In the process for producing vinyl chloride monomer according to the present invention, a portion of the anhydrous hydrogen chloride may be unreacted in the electrochemical cell. This unreacted portion exits the electrochemical cell, along with the essentially dry chlorine gas, and is sent to a purification unit, such as unit 322. The purification unit separates out the unreacted anhydrous hydrogen chloride. The present invention thus may further include the step of recycling the unreacted anhydrous hydrogen chloride to the anode-side inlet of the electrochemical cell through a recycle line, such as line 324 as shown in FIG. 4.

Additional advantages and modifications will readily occur to those skilled in the art. The invention, in its broader aspects, is therefore not limited to the specific details and representative apparatus shown and described. Accordingly, departures may be made from such details without departing from the spirit or scope of the general inventive concept as defined by the appended claims and their equivalents.

What is claimed is:

1. A system for producing ethylene dichloride from chlorine gas produced by the electrochemical conversion of anhydrous hydrogen chloride, comprising:
   (a) a direct chlorination reactor;
   (b) a first inlet supply line for supplying ethylene to the direct chlorination reactor;
   (c) a second inlet supply line for supplying chlorine to the direct chlorination reactor, wherein the ethylene and the chlorine react in the direct chlorination reactor to produce ethylene dichloride;
   (d) an electrochemical cell, including:
      (i) means for oxidizing anhydrous hydrogen chloride to produce chlorine gas and (ii) an anode chamber disposed adjacent the oxidizing means, anode-side inlet means for introducing the anhydrous hydrogen chloride to the oxidizing means and anode-side outlet means also disposed in fluid communication with the anode chamber for discharging the chlorine gas,
      (iii) cation-transporting means for transporting the protons therethrough, wherein the oxidizing means is disposed in contact with one side of the cation-transporting means,
      (iv) means for reducing the transported protons, wherein the reducing means is disposed in contact with the other side of the cation-transporting means, and
      (iv) a cathode chamber disposed adjacent the reducing means, cathode-side inlet means disposed in fluid communication with the cathode chamber for introducing a fluid to the other side of the cation-transporting means and cathode-side outlet means also disposed in fluid communication with the cathode chamber;
   (e) a purification unit for liquefying the chlorine gas to form liquid dry chlorine; and
   (f) a recycle line connected to the anode side outlet means of the electrochemical cell, at one end thereof, and to the second inlet supply line of the direct chlorination reactor, at the other end thereof, for recycling the chlorine to the direct chlorination reactor.

2. The system of claim 1, further including an ethylene dichloride purification unit connected to the direct chlorination unit for purifying the ethylene dichloride.

3. A system for producing vinyl chloride monomer from chlorine gas produced by the electrochemical conversion of anhydrous hydrogen chloride, comprising:
   (a) a direct chlorination reactor;
   (b) a first inlet supply line for supplying ethylene to the direct chlorination reactor;
   (c) a second inlet supply line for supplying chlorine to the direct chlorination reactor, wherein the ethylene and the chlorine react in the direct chlorination reactor to produce ethylene dichloride;
   (d) a pyrolysis unit for pyrolyzing the ethylene dichloride to produce vinyl chloride monomer;
   (e) an electrochemical cell, including:
      (i) means for oxidizing anhydrous hydrogen chloride to produce chlorine gas and protons,
      (ii) an anode chamber disposed adjacent the oxidizing means, anode-side inlet means for introducing the anhydrous hydrogen chloride to the oxidizing means and anode-side outlet means also disposed in fluid communication with the anode chamber for discharging the chlorine gas,
      (iii) cation-transporting means for transporting the protons therethrough, wherein the oxidizing means is disposed in contact with one side of the cation-transporting means,
      (iv) means for reducing the transported protons, wherein the reducing means is disposed in contact with the other side of the cation-transporting means, and
      (v) a cathode chamber disposed adjacent the reducing means, cathode-side inlet means disposed in fluid communication with the cathode chamber for introducing a fluid to the other side of the cation-transporting means and cathode-side outlet means also disposed in fluid communication with the cathode chamber;
   (f) a purification unit for liquefying the chlorine gas to form liquid dry chlorine; and
   (g) a recycle line connected to the anode side outlet means of the electrochemical cell, at one end thereof, and to the second inlet supply line of the direct chlorination reactor, at the other end thereof, for recycling the chlorine to the direct chlorination reactor.

4. The system of claim 3, further including a chlorine supply line disposed in communication with the second supply line for supplying liquid dry chlorine to the second inlet supply line.

5. The system of claim 3, further including an ethylene dichloride purification unit connected to the direct chlorination unit for purifying the ethylene dichloride.

6. The system of claim 5, further including a vinyl chloride monomer purification unit connected to the ethylene dichloride purification unit for purifying the vinyl chloride monomer and for separating the vinyl chloride monomer from the anhydrous hydrogen chloride.

7. The system of claim 6, wherein a portion of the ethylene dichloride is unreacted in the pyrolysis unit, further including a recycle line connected to the vinyl chloride monomer purification unit for recycling the unreacted ethylene dichloride to the ethylene dichloride purification unit.

8. The system of claim 7, wherein a portion of the anhydrous hydrogen chloride is unreacted in the electrochemical cell and is sent to the purification unit, further including a recycle line connected to the purification unit for recycling the unreacted anhydrous hydrogen chloride to the electrochemical cell.

9. A process for producing ethylene dichloride from chlorine gas produced by the electrochemical conversion of anhydrous hydrogen chloride, comprising the steps of:

(a) supplying ethylene to a direct chlorination reactor;

(b) supplying chlorine to the direct chlorination reactor, wherein the ethylene reacts with the chlorine in the direct chlorination reactor to form ethylene dichloride;

(c) supplying anhydrous hydrogen chloride to an anode-side inlet of an electrochemical cell wherein the electrochemical cell comprises a cation-transporting membrane, an anode disposed in contact with one side of the membrane and a cathode disposed in contact with the other side of the membrane;

(d) applying a voltage to the electrochemical cell so that the anode is at a higher potential than the cathode and so that:

(i) the anhydrous hydrogen chloride is oxidized at the anode to produce chlorine gas and protons, (ii) the chlorine gas is released from an anode-side outlet of the cell, (iii) the protons are transported through the cation-transporting membrane of the cell, and (iv) the transported protons are reduced at the cathode of the cell;

(e) liquefying the chlorine gas to form liquid dry chlorine; and (f) recycling the chlorine gas back to the direct chlorination reactor to produce ethylene dichloride.

10. The process of claim 9, wherein a portion of the anhydrous hydrogen chloride is unreacted when it is released from the anode-side outlet of the electrochemical cell, further including the step of recycling the unreacted anhydrous hydrogen chloride to the anode-side inlet of the electrochemical cell.

11. A process for producing vinyl chloride monomer from chlorine gas produced by the electrochemical conversion of anhydrous hydrogen chloride, comprising the steps of:

(a) supplying ethylene to a direct chlorination reactor;

(b) supplying chlorine to the direct chlorination reactor, wherein the ethylene reacts with the chlorine in the direct chlorination reactor to form ethylene dichloride;

(c) pyrolyzing the ethylene dichloride to produce vinyl chloride monomer and anhydrous hydrogen chloride;

(d) supplying the anhydrous hydrogen chloride to an anode-side inlet of an electrochemical cell, wherein the electrochemical cell comprises a cation-transporting membrane, an anode disposed in contact with one side of the membrane and a cathode disposed in contact with the other side of the membrane;

(e) applying a voltage to the electrochemical cell so that the anode is at a higher potential than the cathode and so that:

(i) the anhydrous hydrogen chloride is oxidized at the anode to produce chlorine gas and protons, (ii) the chlorine gas is released from the cell, (iii) the protons are transported through the membrane of the cell, and (iv) the transported protons are reduced at the cathode of the cell;

(f) liquefying the chlorine gas to form liquid dry chlorine; and (g) recycling the liquid dry chlorine to the direct chlorination reactor.

12. The process of claim 11, further including the step of supplying a fresh supply of liquid dry chlorine to the second inlet supply line of the direct chlorination reactor.

13. The process of claim 11, further including the step of purifying the ethylene dichloride in an ethylene dichloride purification unit before the ethylene dichloride is pyrolyzed.

14. The process of claim 13, further including the step of separating the anhydrous hydrogen chloride from the vinyl chloride monomer in a vinyl chloride monomer purification unit.

15. The process of claim 14, further including the step of purifying the vinyl chloride monomer in a vinyl chloride monomer purification unit.

16. The process of claim 15, wherein a portion of the ethylene dichloride is unreacted in the pyrolysis unit, further including the step of recycling the unreacted ethylene dichloride from the vinyl chloride monomer purification unit back to the ethylene dichloride purification unit.

17. The process of claim 11, wherein a portion of the anhydrous hydrogen chloride is unreacted when it is released from the anode-side outlet of the electrochemical cell, further including the step of recycling the unreacted anhydrous hydrogen chloride to the anode-side inlet of the electrochemical cell.

\* \* \* \* \*

UNITED STATES PATENT AND TRADEMARK OFFICE
CERTIFICATE OF CORRECTION

PATENT NO. : 5,891,318
DATED : April 6, 1999
INVENTOR(S) : Francisco Jose Freire et al.

It is certified that error appears in the above-identified patent and that said Letters Patent is hereby corrected as shown below:

IN THE CLAIMS:

Claim 1, (d), (i), line 2, after "and" insert --protons,--.

Claim 1, the second "(iv)" should be --(v)--.

Signed and Sealed this

Twenty-seventh Day of March, 2001

Attest:

NICHOLAS P. GODICI

Attesting Officer

Acting Director of the United States Patent and Trademark Office